United States Patent [19]

Bowie et al.

[11] 4,017,420

[45] Apr. 12, 1977

[54] STABLE OXIDASE REAGENT SOLUTIONS

[75] Inventors: Betty Anne Bowie, Havertown; Joseph F. Pagano, Paoli, both of Pa.

[73] Assignee: SmithKline Corporation, Philadelphia, Pa.

[22] Filed: Dec. 22, 1975

[21] Appl. No.: 643,465

[52] U.S. Cl. .............................. 252/408; 23/230 B; 195/103.5 R; 424/12; 424/13
[51] Int. Cl.$^2$ .......................................... C09K 3/00
[58] Field of Search ................. 252/408; 23/230 B; 195/103.5 R; 424/12, 13

[56] References Cited

UNITED STATES PATENTS 3,876,503   4/1975   Mennen ....................... 195/103.5 R Primary Examiner—Benjamin R. Padgett
Assistant Examiner—E. Suzanne Parr
Attorney, Agent, or Firm—Joseph A. Marlino; Richard D. Foggio; William H. Edgerton

[57] ABSTRACT

Stable oxidase reagent solutions containing N,N,N',N'-tetramethyl-p-phenylenediamine or N,N-dimethyl-p-phenylenediamine for determining the presence of oxidase in microbial colonies.

4 Claims, No Drawings

STABLE OXIDASE REAGENT SOLUTIONS

This invention relates to novel anhydrous oxidase reagent solutions particularly useful in confirming Neisseria colonies which produce the enzyme cytochrome oxidase.

It is well known to employ an oxidase reagent solution for confirming the presence of Neisseria colonies, such as *Neisseria gonorrhoeae* or *Neisseria meningitidis*. The U.S. Public Health Service has established criteria for presumptive and confirmatory identification of *N. gonorrhoeae*. For presumptive diagnosis the organism cultured on a selective medium for *N. gonorrhoeae* must be identified as oxidase positive, Gram negative diplococci exhibiting typical colonial morphology. To further confirm the diagnosis, sugar fermentations and/or fluorescent antibody tests must also be performed.

According to standard laboratory procedures for testing *N. gonorrhoeae*, specimens are obtained with a sterile swab. The sides and tip of the swab are then rolled on a selective medium. A typical solid culture medium for use to culture *N. gonorrhoeae* is disclosed by Martin, J. E., Jr. and Lester A. in HSMHS Health Reports 86: 30–33, 1971. The medium is then incubated for 24–48 hours and inspected for colony growth. Suspect *N. gonorrhoeae* colonies are subjected to an oxidase test to determine if the enzyme cytochrome oxidase is produced. An oxidase positive test reaction is recognized by the development of a dark purple color in 5 to 30 seconds. If careful examination of the medium does not reveal any growth, oxidase reagent is applied to the entire medium. This aids in visualization of pinpoint oxidase-positive colonies that might otherwise be overlooked. Growth of the oxidase positive colonies provides reliable preliminary evidence of *N. gonorrhoeae*. For positive identification, the untreated colonies on the medium or a second untreated culture is subjected to further laboratory confirmatory procedures, i.e., sugar fermentation and fluorescent antibody testing.

The prior art and commercial oxidase reagent used to confirm the presence of Neisseria colonies consists of a 1% aqueous solution of N,N,N',N'-tetramethyl-p-phenylenediamine dihydrochloride. The solution is very unstable. It has a light blue color when freshly prepared and turns to a black color within two or three days and is no longer effective for the detection of oxidase because of the rapid deterioration of the diamine salt. For this reason, it is recommended that the commercial reagent solution be prepared daily.

Because of the unstable nature of the prior art oxidase reagent, it is also recommended that it be kept under a nitrogen atmosphere and in a hermetically sealed glass vial if it is not to be used promptly. Further, the natural blue color of the reagent which deepens upon standing conflicts with the deep purple color obtained when the reagent is applied to the Neisseria organisms and confuses the clinician.

It is therefore the object of this invention to prepare a colorless stable oxidase reagent solution for the detection of microbial colonies which has a relatively long shelf life.

The novel oxidase reagent composition of this invention unexpectedly overcomes the stability problems associated with the prior art oxidase reagent.

The oxidase reagent solution of this invention is colorless and stable. For example, the reagent solution of this invention remains colorless up to eight weeks and retains excellent activity. The solution may be placed in dropper bottles and the need for packaging under nitrogen atmosphere is eliminated.

Furthermore, the stable anhydrous oxidase reagent solution of this invention also provides for a much better contrast between the colonies and the medium. The employment of a colorless solution as the starting material greatly simplifies the visualization and interpretation of the colonies which turn dark purple in the presence of the reagent solution.

The stable anhydrous oxidase reagent solution of this invention is comprised of tetramethyl or dimethyl-p-phenylenediamine in dimethyl sulfoxide. The phenylenediamine will be in an amount of from about 0.1% to about 1.0% by weight of the composition. Preferably the phenylenediamine will be present in an amount of from about 0.2% to about 0.5%. Most advantageously, the stable reagent solution of this invention will contain N,N,N',N'-tetramethyl-p-phenylenediamine.

This invention also includes nontoxic pharmaceutically acceptable addition salts of the above defined bases formed with organic and inorganic acids. Such salts are easily prepared by methods known to the art. The base is reacted with either the stoichiometric amount of organic or inorganic acid in aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, succinic, acetic, propionic, tartaric, salicylic, citric, stearic and palmitic. Exemplary of such inorganic salts are those with hydrochloric, hydrobromic, sulfuric, phosphoric and nitric acids. These salts may also be prepared by the classical method of double decomposition of appropriate salts which is well known to the art.

The following examples specifically illustrate the coloring composition of this invention and will make obvious to one skilled in the art the full practice of the method of the invention.

EXAMPLE 1

| Ingredients | Amounts | |
|---|---|---|
| N,N,N',N'-tetramethyl-p-phenylenediamine | 0.300 | gms. |
| Dimethyl sulfoxide, q.s. | 100.000 | ml. |

The free base is dissolved in the dimethyl sulfoxide to yield a clear, colorless solution.

EXAMPLE 2

| Ingredients | Amounts | |
|---|---|---|
| N,N,N',N'-tetramethyl-p-phenylenediamine dihydrochloride | 0.500 | gms. |
| Dimethyl sulfoxide, q.s. | 100.000 | ml. |

The dihydrochloride salt is dissolved in the dimethyl sulfoxide to yield a clear, colorless solution.

EXAMPLE 3

| Ingredients | Amounts | |
| --- | --- | --- |
| N,N,dimethyl-p-phenylenediamine | 1.0 | gm. |
| Dimethyl sulfoxide, q.s. | 100.0 | ml |

The base is dissolved in the dimethyl sulfoxide.

What is claimed is:

1. A stable oxidase reagent solution for detection of microbial colonies comprising from about 0.1% to about 1.0% by weight of N,N,N',N'-tetramethyl-p-phenylenediamine or N,N-dimethyl-p-phenylenediamine in dimethyl sulfoxide or acid addition salts thereof.

2. The reagent solution of claim 1 wherein the diamine is N,N,N',N'-tetramethyl-p-phenylenediamine.

3. The reagent of claim 2 wherein the diamine is present as the dihydrochloride salt.

4. The reagent solution of claim 1 wherein the diamine is N,N-dimethyl-p-phenylenediamine.

* * * * *